US012691087B2

(12) United States Patent
Cox et al.

(10) Patent No.: US 12,691,087 B2
(45) Date of Patent: Jul. 28, 2026

(54) METHOD OF ENHANCING GLUCOSE LEVELS IN THE CENTRAL NERVOUS SYSTEM

(71) Applicant: THE INSTITUTE FOR ETHNOMEDICINE, Jackson, WY (US)

(72) Inventors: Paul Alan Cox, Jackson, WY (US); Sandra Anne Banack, Jackson, WY (US)

(73) Assignee: THE INSTITUTE FOR ETHNOMEDICINE, Jackson, WY (US)

( * ) Notice: Subject to any disclaimer, the term of this patent is extended or adjusted under 35 U.S.C. 154(b) by 694 days.

(21) Appl. No.: 16/435,154

(22) Filed: Jun. 7, 2019

(65) Prior Publication Data

US 2019/0374493 A1     Dec. 12, 2019

Related U.S. Application Data

(60) Provisional application No. 62/682,594, filed on Jun. 8, 2018.

(51) Int. Cl.
*A61K 31/198* (2006.01)
*A61P 3/08* (2006.01)

(52) U.S. Cl.
CPC .............. *A61K 31/198* (2013.01); *A61P 3/08* (2018.01)

(58) Field of Classification Search
CPC .................................................. A61K 31/198
See application file for complete search history.

(56) References Cited

U.S. PATENT DOCUMENTS

| | | | |
|---|---|---|---|
| 9,072,730 B2 | 7/2015 | Salehi et al. | |
| 2005/0287204 A1 | 12/2005 | Hageman et al. | |
| 2007/0286909 A1 | 12/2007 | Smith et al. | |
| 2008/0171736 A1* | 7/2008 | Gregory ............... | A61K 31/553 |
| | | | 514/297 |
| 2011/0081329 A1 | 4/2011 | Smith et al. | |
| 2013/0005783 A1 | 1/2013 | Hornemann | |
| 2013/0156846 A1 | 6/2013 | Rodgers et al. | |
| 2017/0173166 A1 | 6/2017 | Ben Dror et al. | |
| 2018/0027781 A1 | 2/2018 | Rodgers et al. | |

FOREIGN PATENT DOCUMENTS

| | | |
|---|---|---|
| CN | 103417522 A | 12/2013 |
| CN | 106361738 A | 2/2017 |
| JP | 08-133984 A2 | 5/1996 |
| WO | 02/38141 A2 | 5/2002 |
| WO | 2008/033299 A2 | 3/2008 |
| WO | 2011/0104298 A1 | 9/2011 |
| WO | 2013/078395 A1 | 5/2013 |

OTHER PUBLICATIONS

Fridman et al., Randomized trial of L-Serine in patients with hereditary sensory and autonomic neuropathy type 1, American Academy of Neurology, Jan. 8, 2019, pp. e359-e370, Wolters Kluwer Health, Inc.
Auranen et al., Clinical and metabolic consequences of L-serine supplementation in hereditary sensory and autonomic neuropathy type 1C, Cold Spring Harb Mol Case Stud, 2017, pp. 1-9, 3:a002212.
Atkinson et al., Human memory: A proposed system and its control processes, Psychology of learning and motivation, Dec. 31, 1968; pp. 89-195, vol. 2.
Cox et al., Traditional food items in Ogimi, Okinawa: L-serine content and the potential for neuroprotection, Current Nutrition Reports, Mar. 1, 2017, pp. 24-31, 6(1).
Greely et al., Towards responsible use of cognitive-enhancing drugs by the healthy, Nature, Dec. 7, 2008, pp. 702-705, 456(7223).
Hogervorst et al., The nature of the effect of female gonadal hormone replacement therapy on cognitive function in post menopausal women: a meta-analysis, Neuroscience, Nov. 15, 2000, pp. 485-512, 101(3).
Kasai et al., Transport systems of serine at the brain barriers and in brain parenchymal cells, Journal of Neurochemistry, Jul. 1, 2011, pp. 304-313, 118(2).
Ilieva et al., Objective and subjective cognitive enhancing effects of mixed amphetamine salts in healthy people, Neuropharmacology, 2013, pp. 496-505, 64.
Levine et al., Phase I clinical trial of safety of L-serine for ALS patients, Amyotrophic Lateral Sclerosis and Frontotemporal Degeneration, Jan. 2, 2017, pp. 107-111, 18(1-2).
Berger et al., Postoperative Cognitive Dysfunction, Minding the Gaps in Our Knowledge of a Common Postoperative Complication in the Elderly, Anesthesiol Clin., Sep. 2015, pp. 517-550, 33(3).
Crook et al., Age-associated memory impairment: Proposed diagnostic criteria and measures of clinical change report of a national institute of mental health work group, Developmental Neuropsychology, 1986, pp. 261-276, 2:4.
Cunnane et al., Brain fuel metabolism, aging, and Alzheimer's disease, Nutrition, 2011, pp. 3-20, vol. 27.
Dekoning et al., L-Serine in disease and development, Biochem, J., 2003, pp. 653-661, vol. 371.
Dekoning et al., Serine-deficiency syndromes, Current Opinion in Neurology, 2004, pp. 197-204, vol. 17.
De Vivo et al., Defective Glucose Transport Across the Blood-Brain Barrier as a Cause for Persistent Hypoglycorrhachia, Seizures, and Developmental Delay, The New England Journal of Medicine, Sep. 5, 1991, pp. 703-709, vol. 325(10).

(Continued)

*Primary Examiner* — Yong S. Chong

(74) *Attorney, Agent, or Firm* — Pillsbury Winthrop Shaw Pittman, LLP

(57) ABSTRACT

Presented herein are compositions and uses thereof for: (i) increasing or regulating glucose concentration in a central nervous system of a subject, (ii) inhibiting or delaying cognitive decline in a subject, (iii) enhancing cognitive function in a subject, and/or (iv) treating a disease or condition associated with a decreased level of glucose in a central nervous system of a subject. In some embodiments, the compositions provided herein comprise L-serine, or a precursor, derivative or conjugate thereof.

15 Claims, 1 Drawing Sheet

(56)            References Cited

OTHER PUBLICATIONS

Duffy et al., Improved cognitive function in postmenopausal women after 12 weeks of consumption of a soya extract containing isoflavones, Pharmacology Biochemistry and Behavior, 2003, pp. 721-729, vol. 75.

Duka et al., The effects of 3-week estrogen hormone replacement on cognition in elderly healthy females, Psychopharmacology, 2000, pp. 129-139, vol. 149.

Gershon et al., NIH Toolbox for Assessment of Neurological and Behavioral Function, American Academy of Neurology, Mar. 12, 2013, pp. S2-S6, vol. 80.

Jacobs et al., Cognitive function in nondemented older women who took estrogen after menopause, Neurology, 1998, pp. 368-373, vol. 50.

King, et al., Detecting Simulated Memory Impairment with the Rey Auditory Verbal Learning Test: Implications of Base Rates and Study Generalizability, Journal of Clinical and Experimental Neuropsychology, 1998, pp. 603-612, vol. 20(5).

Larrabee, Partitioning of CO2 Production Between Glucose and Lactate in Excised Sympathetic Ganglia, with Implications for Brain, Journal of Neurochemistry, 1996, pp. 1726-1734, vol. 67.

Lewis et al., The sensitivity and specificity of three common statistical rules for the classification of post-operative cognitive dysfunction following coronary artery bypass graft surgery, Acta Anaesthesiol Scand, 2006, pp. 50-57, vol. 50.

Liu et al., Decreased glucose transporters correlate to abnormal hyperphosphorylation of tau in Alzheimer disease, FEBS Letters, 2008, pp. 359-364, vol. 582.

Metcalf et al., L-Serine: a Naturally-Occurring Amino Acid with Therapeutic Potential, Springer, Sep. 19, 2017, pp. 1-9.

Pascual et al., GLUT1 deficiency and other glucose transporter diseases, European Journal of Endocrinology, 2004, pp. 627-633, vol. 150.

Petersen et al., Mild Cognitive Impairment, Arch Neurol, Mar. 1999, pp. 303-308, p. 760, vol. 56.

Saczynski et al., Cognitive Trajectories after Postoperative Delirium, N Engl J Med, Jul. 5, 2012, 30-39, vol. 367(1).

Sahakian et al., The impact of neuroscience on society: cognitive enhancement in neuropsychiatric disorders and in healthy people, Phil. Trans. R. Soc. B, 2015, pp. 1-13, vol. 370.

Shah et al., The Role of Glucose Transporters in Brain Disease: Diabetes and Alzheimer's Disease, Int. J. Mol. Sci., 2012, pp. 12629-12655, vol. 13.

Van Der Crabben et al., An update on serine deficiency disorders, J Inherit Metab Dis, 2003, pp. 613-619, vol. 36.

Wang et al., Mutational Analysis of GLUT1 (SLC2A1) in Glut-1 Deficiency Syndrome, Human Mutation, 2000, pp. 224-231, vol. 16.

Wolosker et al., Serine racemase: A glial enzyme synthesizing D-serine to regulate glutamate-N-methyl-D-aspartate neurotransmission, PNAS, Nov. 9, 1999, pp. 13409-13414, vol. 96(23).

Yaffe et al., Estrogen Therapy in Postmenopausal Women, JAMA, Mar. 4, 1998, pp. 688-695, vol. 279(9).

Yang et al., Serine and one-carbon metabolism in cancer, Nature Reviews, Oct. 2016, pp. 650-662, vol. 16.

Youngjohn et al., Stability of Everyday Memory in Age-Associated Memory Impairment: A Longitudinal Study, Neuropsychology, 1993, pp. 406-416, vol. 7(3).

ClinicalTrials.gov Identifier: NCT03635229, Risk Factor of POD and POCD After Cardiac Surgery, Mahidol University, Aug. 17, 2018, pp. 1-5, Thailand.

ClinicalTrials.gov Identifier: NCT03029676, The Assessment of POCD After TURBT Under Spinal Anesthesia, Medical University of Warsaw, Jan. 24, 2017, pp. 1-6, Poland.

ClinicalTrials.gov Identifier: NCT02650687, Optimizing Postoperative Cognition the Elderly, Icahn School of Medicine at Mount Sinai, Jan. 8, 2016, pp. 1-6, New York, NY, US.

ClinicalTrials.gov Identifier: NCT02848599, The Influence of Postoperative Analgesia on Systemic Inflammatory Response and POCD After Femoral Fractures Surgery, Osijek University Hospital, Jul. 28, 2016, pp. 1-9, Croatia.

ClinicalTrials.gov Identifier: NCT03540433, International Observational Study on Perioperative Cognitive Trajectories POCD Census International/PCI), Charite University Berlin, May 30, 2018, pp. 1-10, Germany.

ClinicalTrials.gov Identifier: NCT03084393, POCD: Correlations With the Gene Polymorphism and the Concentrations of Plasma Homocysteine, Folic Acid and Vitamin B12., Xuzhou Medical University, Mar. 20, 2017, pp. 1-6, China.

ClinicalTrials.gov Identifier: NCT02265263, Biomarker Development for Postoperative Cognitive Impairment in the Elderly (BioCog) (BioCog), Charite University Berlin, Oct. 15, 2014, pp. 1-11, Germany.

Patent Cooperation Treaty, International Search Report issued in PCT/US2019/036115, Oct. 1, 2019, pp. 1-4.

European Patent Office, Extended European Search Report issued in EP 19815799.2, Feb. 2, 2022, pp. 1-9.

Holm et al., "L-serine supplementation lowers diabetes incidence and improves blood glucose homeostasis in NOD mice", PLOS One, Mar. 15, 2018, pp. 1-15, vol. 13(3).

Kato-Kataoka et al., "Soybean-Derived Phosphatidylserine Improves Memory Function of the Elderly Japanese Subjects with Memory Complaints", J. Clin. Biochem. Nutr., Nov. 2010, p. 246-255, vol. 47.

Stark, National Library of Medicine, ClinicalTrials.gov Identifier: NCT03062449, Phase IIa L-serine Trial for eAD (LSPI-2), Dartmouth-Hitchcock Medical Center, Mar. 1, 2017, pp. 1-12, Lebanon, New Hampshire, United States.

Mann et al., Palmitoyl Serine: An Endogenous Neuroprotective Endocannabinoid-Like Entity After Traumatic Brain Injury, J Neuroimmune Pharmacol, Feb. 27, 2015, pp. 1-8.

Sun et al., "L-Serine Treatment May Improve Neurorestoration of Rats after Permanent Focal Cerebral Ischemia Potentially Through Improvement of Neurorepair", PLOS One, Mar. 26, 2014, vol. 9(3), e93405.

Lall et al., "Serine and threonine beta-lactones: a new class of hepatitis A virus 3C cysteine proteinae inhibitors", J Org Chem., Mar. 2002, pp. 1536-1547, vol. 67(5).

Sim et al., L-Serine Supplementation Attenuates Alcoholic Fatty Liver by Enhancing Homocysteine Metabolism in Mice and Rats, The Journal of Nutrition, Nutrition and Disease, Dec. 10, 2014, pp. 260-267.

Klepper et al., "GLUT1 deficiency syndrome—2007 update", Developmental Medicine & Child Neurology, 2007, pp. 707-716, vol. 49.

Jensen et al., "Cerebrospinal fluid glucose is not altered in patients with dementia", Clinical Biochemistry, Dec. 8, 2022, pp. 1-5, vol. 112.

Pappas et al., "CSF glucose tracks regional tau progression based on Alzheimer's disease risk factors", Alzheimer's & Dementia: Translational Research & Clinical Interventions, Aug. 22, 2020, pp. 1-10, wileyonlinelibrary.com/journal/trc2.

Rosness et al., "Association Between Random Measured Glucose Levels in Middle and Old Age and Risk of Dementia Related Death", JAGS, Jan. 2016, pp. 156-161, vol. 64(1).

* cited by examiner

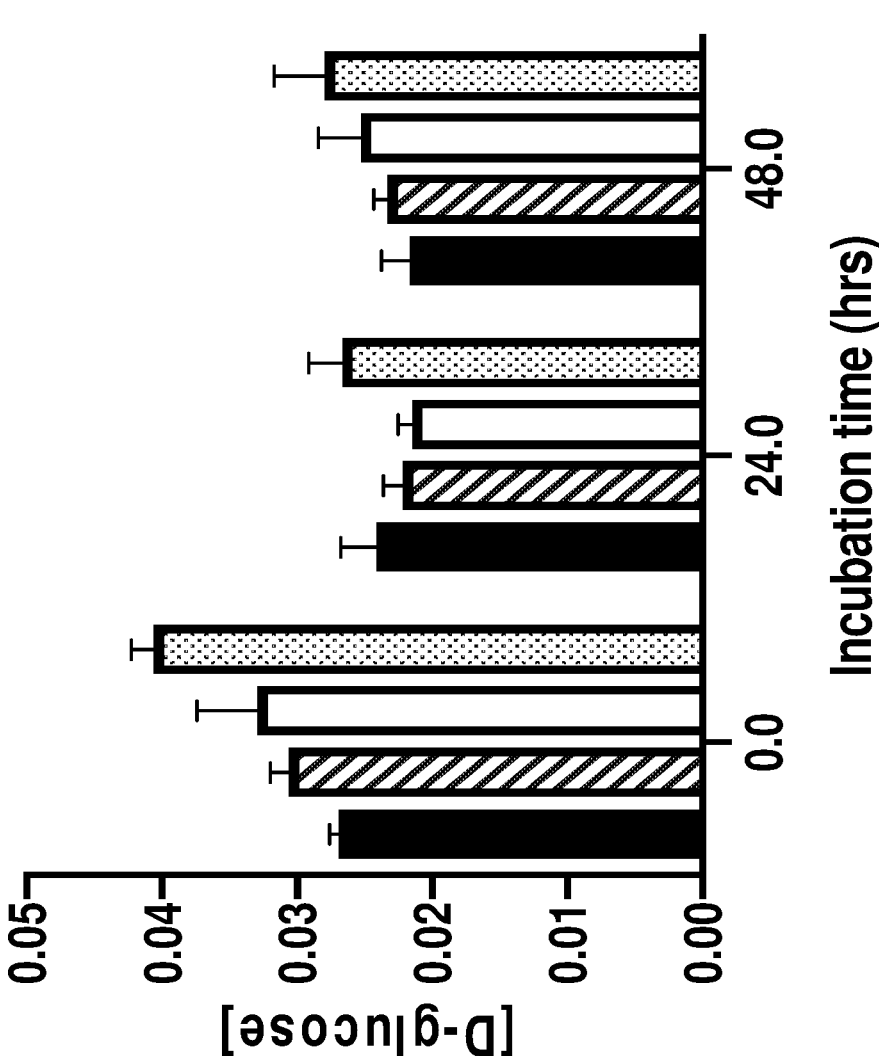

METHOD OF ENHANCING GLUCOSE LEVELS IN THE CENTRAL NERVOUS SYSTEM

RELATED APPLICATIONS

This application claims the benefit of priority of U.S. patent application Ser. No. 62/682,594, entitled "Method of Enhancing Glucose Levels in the Central Nervous System" filed Jun. 8, 2018, which is expressly incorporated herein by reference in its entirety.

BACKGROUND

Glucose is the major fuel for the human brain. Thus, severe neurological consequences can result if glucose transport across the brain is in any way impaired or compromised. Under normal circumstances, the human brain consumes about 120 grams per day of glucose, accounting for 70% of all glucose use by the human body. This fuels a metabolic rate of glucose of 6 mg/100 g, per minute (Cunnane et al., 2011). This consumption of glucose is equivalent to 420 kilocalories of energy input (Berg et al. Biochemistry, 2002).

Improvement of memory and cognitive function can be a significant factor in increased quality of life, economic opportunity, and positive social interactions for many individuals. Prescription cognition-enhancing drugs, such as Adderall and Ritalin, designed to be prescribed as a treatment for attention deficit activity disorder (ADDH), are frequently diverted by students on university campuses, in an effort to increase learning and recall for exams, sometimes with disastrous results including addiction and neuropsychiatric disorders. Double-blind studies show that cognitive enhancement due to Adderall is more self-perceived than based in reality (Ilieva et al. 2013). Modafinil, prescribed for the treatment of narcolepsy and sleep apnea, is also sometimes illicitly used for cognitive enhancement (Greeley et al. 2008). Furthermore, some drugs used to treat cognitive symptoms of Alzheimer's disease, particularly acetylcholinesterase inhibitors, are misused by healthy people in an attempt to enhance cognition (Sahakian et al. 2015).

Cognitive decline is of increasing interest for older populations who experience episodic memory loss. As a result, there have been significant efforts in finding means of improving episodic memory in post-menopausal women who face age-related declines in cognition, including estrogen replacement therapy (Jacobs et al., 1998; Duka et al., 2000; Hogervorst et al., 2000). However, a meta-analysis of ten different studies of estrogen use by post-menopausal women concluded that, given the known risks of estrogen therapy, estrogen is not recommended for the prevention or treatment of AD or other dementias (Yaffe et al., 1998). More recently, soy products, including soya isoflavone supplements, which function as nonsteroidal estrogens, have been tested in post-menopausal women to determine if cognitive function can be improved through their consumption, with no observable impact on menopausal symptoms, mood, or sleepiness, but some advantage in learning rule reversals (Duffy et al., 2003).

The present embodiments disclosed herein provide methods to enhance glucose levels in the central nervous system, including the brain, to address various conditions and diseases and to enhance cognitive function.

SUMMARY

Provided herein, in some aspects, is a method of increasing or regulating glucose concentration in a subject comprising administering to the subject a composition comprising a therapeutically effective amount of L-serine, or a precursor, derivative or conjugate thereof. In some embodiments, a method described herein increases glucose levels in the central nervous system of a subject. In some aspects, provided herein is a method of treating a disease or condition associated with a decreased level of glucose in the central nervous system of a subject comprising administering to the subject a composition comprising a therapeutically effective amount of L-serine, or a precursor, derivative or conjugate thereof. In some embodiments, a method comprises treating a subject having a disease or condition characterized by a decreased amount of glucose in the central nervous system which comprises administering to the subject L-serine at a dose of about 10 to about 60 g/day, or in some embodiments about 10 to about 30, or about 10 to about 15 g/day.

In some aspects, provided herein is a method of inhibiting or delaying cognitive decline in a subject comprising administering to the subject a composition comprising a therapeutically effective amount of L-serine, or a precursor, derivative or conjugate thereof.

In some aspects, provided herein is a method of enhancing cognitive function (i.e., cognitive enhancement), comprising administering to a subject a composition comprising a therapeutically effective amount of L-serine, or a precursor, derivative or conjugate thereof.

In some aspects, provided herein is a method of treating a disease or condition associated with, or caused by, impaired glucose transport into the brain of a subject, the method comprising administering to the subject a composition comprising a therapeutically effective amount of L-serine, or a salt, a precursor, derivative or conjugate thereof.

In some aspects, provided herein is a method of improving learning ability in subject, the method comprising administering to the subject L-serine, or a salt, a precursor, derivative or conjugate thereof. In some embodiments, a method of improving learning ability in humans, as measured by the Rey Auditory Verbal Learning Test, comprises administering to the human subject L-serine at a dose of about 10 to about 15 g/day.

BRIEF DESCRIPTION OF THE DRAWINGS

FIG. 1 is a bar graph showing the concentration of D-glucose (y-axis; mM) in the culture media of human neuroblastoma cells (SH-SY5Y) treated with 0 mM (control), 100 mM, 200 mM and 500 mM L-serine for a period of 0, 24 or 48 hours (x-axis).

DETAILED DESCRIPTION

Embodiments disclosed herein generally relate to the use of L-serine, or a salt, a precursor, derivative or conjugate thereof, to increase or regulate concentrations of glucose within a subject (e.g., in the central nervous system (CNS) of a subject), to prevent, treat, delay the onset of, and\or inhibit or reduce one or more symptoms of certain diseases, conditions and\or disorders disclosed herein and\or to improve memory, learning and\or cognitive function. In some embodiments, a method disclosed herein comprises administering a composition comprising L-serine, or a salt, a precursor, derivative or conjugate thereof, to a subject. In some embodiments, a method disclosed herein comprises administering L-serine, or a salt, a precursor, derivative or conjugate thereof, to a subject.

Diseases and Conditions

In certain aspects, provided herein are methods of preventing, treating, delaying the onset of, and\or inhibiting or reducing one or more symptoms of a disease or condition associated with, or caused by, a decreased level of glucose in a subject (e.g., the central nervous system of a subject), non-limiting examples of which include GLUT1 deficiency syndrome, epilepsy, post-operative cognitive dysfunction, glucose-6-phosphate dehydrogenase (G6PD) deficiency, GLUT2 deficiency, GLUT3 deficiency, SGLT1 deficiency, SGLT2 deficiency, Fanconi-Bickel syndrome, glucose-galactose malabsorption syndrome, aldolase A deficiency, Downs syndrome, hypoglycemia, alcoholism, hepatitis, anorexia, insulinoma, Mild Cognitive Impairment (MCI), amnestic MCI (aMCI), Age-Associated Memory Impairment (AAMI), Age Related Cognitive Decline (ARCO), chemotherapy-induced cognitive dysfunction and attention deficit hyperactivity disorder (ADHD), and other age-related or neurodegenerative diseases. In some embodiments, a disease or condition that can be treated by a method herein comprises hypoglycemia. In certain embodiments, a disease or condition that can be treated by a method herein comprises diabetes (e.g., Type I diabetes or Type II diabetes) or insulin resistance.

In certain embodiments, a method comprises preventing, treating, delaying the onset of, and\or inhibiting, suppressing or reducing one or more symptoms of Mild Cognitive Impairment (MCI). In certain embodiments, a method comprises enhancing memory in a subject having, or suspected of having, Mild Cognitive Impairment (MCI). Mild Cognitive Impairment (MCI) often refers to a condition characterized by isolated memory impairment unaccompanied by other cognitive abnormalities, conditions, diseases or deficiencies. Other than memory impairment, a subject having MCI often displays relatively normal physical and cognitive function. In some embodiments, a subject having MCI comprises one or more of the following characteristics: (1) loss of memory complaint (as reported by patient, informant, or physician), (2) otherwise normal activities of daily living (ADLs), (3) otherwise normal global cognitive function, (4) abnormal memory for age (defined as scoring more than 1.5 standard deviations below the mean for a given age), and (5) absence of indicators of dementia (as defined by DSM-IV guidelines). In some embodiments, a determination or diagnosis of MCI in a subject can be made by a method described in Petersen et al., Srch. Neurol. 56: 303-308 (1999); Petersen, "Mild cognitive impairment: Aging to Alzheimer's Disease." Oxford University Press, N.Y. (2003). Accordingly, in some embodiments, a subject having, or suspected of having MCI is a subject that is not diagnosed with, and\or does not have Amyotrophic Lateral Sclerosis (ALS), Alzheimer's disease (AD), Amyotrophic Lateral Sclerosis/Parkinsonism Dementia Complex (ALS\PDC), dementia, Parkinson's Disease (PD), Huntington's disease (HD), Progressive Supranuclear Palsy (PSP), and\or Levy Body Dementia (LBD).

In some embodiments, a method comprises preventing, treating, delaying the onset of, and\or inhibiting, suppressing or reducing one or more symptoms of Age-Associate Memory Impairment (AAMI). In certain embodiments, a method comprises enhancing memory in a subject having, or suspected of having AAMI. Age-Associate Memory Impairment (AAMI) often refers to a decline in memory due to aging. In some embodiments, AAMI refers to subjects with objective memory decline relative to their younger years, but cognitive function that is normal relative to their age peers (e.g., see Crook et al., 1986). In some embodiments, a subject having AAMI, or suspected of having AAMI is at least 50 years old and comprises one or more of the following characteristics; a) the subject has noticed a decline in memory performance, b) the subject performs worse on a standard test of memory compared to young adults, c) all other obvious causes of memory decline, except normal aging, have been ruled out (in other words, the memory decline is not attributed to other causes such as a recent heart attack or head injury, depression, adverse reactions to medication, Alzheimer's disease, ALS, etc.). In some embodiments, a subject having, or suspected of having AAMI is a subject that is not diagnosed with, and\or does not have ALS, AD, ALS\PDC, dementia, PD, HD, PSP, and\or LBD.

In some embodiments, a method comprises preventing, treating, delaying the onset of, and\or inhibiting, suppressing or reducing one or more symptoms of Age-Related Cognitive Decline (ARCD). In certain embodiments, a method comprises enhancing memory and\or learning in a subject having, or suspected of having ARCD. ARCD often refers to a decline in memory and cognitive abilities that are a normal consequence of aging in humans (e.g., Craik & Salthouse, 1992). In some embodiments, a subject having or suspected of having ARCD is a subject that is at least 50 years old, at least 55 years old, at least 60 years old, at least 65 years old or at least 70 years old. ARCD is sometimes referred to as Age-Consistent Memory Decline, a less pejorative label, which emphasizes that these are normal developmental changes (e.g., see Crook, 1993; Larrabee, 1996), are not pathophysiological (e.g., see Smith et al., 1991), and rarely progress to overt dementia (e.g., see Youngjohn & Crook, 1993). In some embodiments, a subject having, or suspected of having ARCD is a subject that is not diagnosed with, and\or does not have ALS, AD, ALS\PDC, dementia, PD, HD, PSP, and\or LBD.

In certain aspects, provided herein are methods of preventing, inhibiting, reducing, suppressing, slowing or delaying cognitive decline, cognitive disfunction, and/or loss of memory in a subject, the method comprising administering to the subject a composition comprising a therapeutically effective amount of L-serine, or a salt, a precursor, derivative or conjugate thereof. In some embodiments, a method herein inhibits, reduces, suppresses or delays cognitive decline, cognitive disfunction, and/or loss of memory by an amount of about at least 5%, 10%, 15%, 20%, 25%, 35%, 40%, 45%, 50%, such as from about 1% to 100%, from 2% to 100%, from 5% to 100%, from 10% to 100%, from 20% to 100%, from 30% to 100%, or from about 40% to 100%. In some embodiments, an inhibition of cognitive decline or loss of memory is an improvement in cognitive ability and/or an increase in memory. In some embodiments, an inhibition of cognitive decline is an absence of further cognitive decline, or in some embodiments, no change in cognitive decline. In some embodiments, an inhibition of loss of memory is an absence of further loss of memory, or in some embodiments, no change in memory.

In some embodiments, cognitive function, or changes in cognitive function (e.g., improvements thereof, or a decline thereof) includes a suitable subjective or objective assessment of a subject's cognitive function. In some embodiments, cognitive function (e.g., including memory and learning) and/or changes in cognitive function (e.g., cognitive decline, cognitive impairment, loss of memory, enhanced learning ability) is determined by, or assessed by a subject's performance in one or more suitable cognitive tests, non-limiting examples of which include measures of attention, processing speed, executive function, social interaction, fine motor skills, speech, physical ability to move, memory, psychometric tests, neurological tests, problem solving tests, counting tests, language tests, global ability, combinations thereof, and the like. Additional non-limiting examples of cognitive tests that can be used to assess cognitive function include the Mini-Mental State Examination (MMSE) (e.g., see Saczynski et al., (2012) N. Engl. J. Med. 367:30-39); the Reliable Change Index (e.g., see Lewis et al., (2006) Acta Anaesthesiol Scand. 50:50-57; and Berger et al., (2015) Anesthesiol Clin. 33(3):517-50); the Rey Auditory Verbal Learning Tests; Trail Making Tests, Parts A & B; the Grooved Peg Board Test; the Digit Span Tests; the Stroop Tests, the Four-Field Tests, Erzigkeit's Short Cognitive Performance Test; a patients self-assessment; as well as a variety of tests disclosed in various clinical trials (e.g., see ClinicalTrials.gov Identifier: NCT0361019, NCT03540433, NCT02265263, NCT02650687, NCT02848599, NCT03084393, NCT03029676 and NCT03635229). In certain embodiments, cognitive function, or changes thereof, is measured by comparing the results of a suitable medical evaluation or cognitive test conducted before and/or after administering a composition disclosed herein. Non-limiting examples of medical evaluations include brain computed tomography (CT), magnetic resonance imaging (MRI) scans, single photon emission computed tomography (SPECT), PET scans, and the like.

In some embodiments, cognitive decline is self-reported by a subject (e.g., complains of memory loss), or through observation of a subject's behavior.

In certain aspects, provided herein are methods of enhancing cognitive function (e.g., an increase in cognitive function; cognitive enhancement) in a subject, the method comprising administering to the subject a composition containing a therapeutically effective amount of L-serine, or a salt, a precursor, derivative or conjugate thereof. Non-limiting examples of enhancing cognitive function include an increase in memory and\or an increase in learning. In some embodiments, an enhancement of cognitive function is demonstrative by an increase in the level of at least one aspect of coanitive function over a baseline level prior to conducting a method described herein. In some embodiments, cognitive enhancement is achieved in a subject when the subject shows improvement in one or more tests of cognitive function after completion of a method disclosed herein. For example, in some embodiments, cognitive enhancement is achieved in a subject when a subject's memory or learning ability is enhanced compared to an amount of memory or learning ability prior to administration of a composition described herein. In some embodiments, cognitive enhancement is assessed by comparison to a placebo treatment.

In some embodiments, a method described herein enhances cognitive function in healthy subjects by administering L-serine, or a salt, a precursor, derivative or conjugate thereof. In certain Examples disclosed herein, it was determined that dietary supplementation with L-serine can improve cognitive function (e.g., learning and/or memory) in healthy subjects, non-limiting examples of which include a subject that does not have, or is not diagnosed with disease, disorder or condition associated with a decline in, a loss of, or a deficit in cognitive function.

In some embodiments, a method comprises supplementing, increasing, or elevating an amount or level of glucose in a subject (e.g., in the CNS or brain of a subject). In some embodiments, a method comprises preventing, inhibiting, delaying the onset of, treating, or reducing one or more symptoms of a disease or conditions caused by or associated with a deficiency of a glucose transporter. In certain embodiments, a deficiency of a glucose transporter includes a deficiency in expression or function of a glucose transporter, or a decreased level of a glucose transporter.

Glucose is actively transported across the blood brain barrier by transporter proteins by a saturable process. Glucose transporters are membrane proteins that facilitate the transport of glucose across the plasma membrane. Non-limiting examples of glucose transporters include sodium-independent glucose transporter (GLUT) 1 to 14 (e.g., GLUT1, GLUT2, GLUT2, GLUT4, and the like), sodium-dependent glucose transporter (SGLT) 1 and 2 (e.g., see Shah et al., 2012)(i.e., SGLT1 and SGLT2). Availability of glucose to the central nervous system is sometimes limited by an absence of, or a deficiency of, transporters which shuttle glucose across the blood brain barrier. Active transport of glucose across the blood brain barrier is often necessary for normal brain functioning. However, mutations in genes coding for glucose transporters, or sometimes degradation of glucose transporter proteins by environmental toxins can interfere with proper provisioning of glucose to the brain.

The glucose transporter GLUT1 is abundant in tissues associated with the blood brain barrier. Mutations associated with GLUT1 can result in suboptimal levels of glucose in the CNS (De Vivo et al., 1991). Other glucose transporters across the blood brain barrier, including GLUT3, GLUT4, SGLT1, and SGLT2 may play important roles in proper development of the central nervous system or in maintenance of neuronal health and neuronal repair in the aftermath of serious illnesses including diabetes or ischemic stroke.

Glucose transport across the blood brain barrier can be impaired in the case of Alzheimer's disease, other neurodegenerative diseases, epilepsy, and ischemic stroke (Shah et al., 2012). Two glucose transporters, GLUT1 and GLUT3, are decreased in brain tissues from Alzheimer's disease patients (Liu et al., 2008). It is believed that altered glucose transport associated with aging may play an important role in Alzheimer's disease, and that decreased glucose transporters are associated with hyperphosphorylation of tau in Alzheimer's disease (Liu et al., 2008).

Neurological consequences of inadequate glucose transport across the blood brain barrier are not limited to the aged. GLUT1 deficiency is a genetic abnormality in the glucose transporter molecule that occurs in small children. GLUT1 deficiency falls into a broader class of glucose transporter diseases (Pascual et al., 2004) including Fanconi-Bickel syndrome and glucose-galactose malabsorption syndrome.

De Vivo's disease (also known as GLUT1 deficiency syndrome) was first described in 1991 (De Vivo et al., 1991). Genetic analysis of 15 children with GLUT1 deficiency syndrome indicates a variety of mutations in the GLUT1 transporter protein (Wang et al., 2000). Children with GLUT1 deficiency syndrome have clinical manifestations of seizures, delayed development, and microcephaly. About 4,000 children in the United States suffer from this disease, with perhaps 30,000-40,000 cases occurring worldwide.

In some embodiments, the methods described herein enhance glucose levels in the central nervous system, brain or CSF by administering L-serine to a subject. Without being limited to theory, administration of L-serine may provide the CNS with alternative methods of producing glucose.

In some embodiments, a method comprises supplementing, increasing, or elevating an amount or level of glucose in a subject. In some embodiments, an amount or level of glucose in a subject refers to an amount or level of glucose in a bodily fluid of a subject, non-limiting examples of which include blood, plasma, lymph and cerebral spinal fluid. In some embodiments, a method comprises supplementing, increasing, or elevating an amount or level of glucose in the central nervous system of a subject. Accordingly, in some embodiments, a method comprises supplementing, increasing, or elevating an amount or level of glucose in brain, intracranial region and\or cerebral spinal fluid (CSF) of a subject. In some embodiments, a method comprises increasing or elevating an amount or level of glucose in a subject relative to an amount or level of glucose in the subject prior to conducting a method herein, for example, prior to administering a composition comprising L-serine, or a salt, a precursor, derivative or conjugate thereof, to the subject. In some embodiments, a method comprises increasing or elevating an amount or level of glucose in a subject to an amount or level of glucose in the subject that is equal to or greater than an amount or level of glucose considered to be normal in a healthy subject. In certain embodiments, the administration of a composition disclosed herein containing a therapeutically effective amount of L-serine, or a salt, a precursor, derivative or conjugate thereof, can increase the level of glucose in the CNS of a subject. Without being limited to theory, in some embodiments, the administration of a composition disclosed herein containing a therapeutically effective amount of L-serine, or a salt, a precursor, derivative or conjugate thereof, can increase the level of glucose in the CNS of a subject by reversing (e.g., driving backwards) the normal L-serine biosynthetic pathway in astrocytes and other glial cells. Without being limited to theory, in some embodiments, the administration of a composition disclosed herein containing a therapeutically effective amount of L-serine, or a salt, a precursor, derivative or conjugate thereof, can increase intracranial glucose by reversing the typical phosphoglycerate dehydrogenase (PHGDH) pathway for biosynthesis of L-serine within astrocytes in the CNS. As disclosed in the Examples herein, non-human primates given oral dosing with L-serine displayed significantly increased glucose levels in the CNS.

In some embodiments, a normal amount or level of glucose in a healthy subject is disclosed in, and\or can be determined by a method disclosed in Graff's Textbook of Routine Urinalysis and Body Fluids, second edition (2010) by Mundt & Shanahan; Lippincott Williams & Wilkins, Philadelphia, PA and/or in Principles of neurologic infectious diseases (2005) by Roos; McGraw-Hill, Medical Pub. Division, New York. In some embodiments, a normal level of glucose in CSF of a healthy human subject is in a range of 2.5 and 4.4 mmol/L (45-80 mg/dL), or about 2 to 4 mmol/L. Accordingly, in some embodiments, a method comprises supplementing, increasing, or elevating an amount or level of glucose in the central nervous system of a subject from a level below about 1.5 mmol/L, below about 1.8 mmol/L, below about 2.0 mmol/L, below about 2.2 mmol/L, or below about 2.5 mmol/L, to a level in a range of about 2 mmol/L or higher, 2.2 mmol/L or higher, 2.5 mmol/L or higher, 3 mmol/L or higher, 3.5 mmol/L or higher, 4 mmol/L or higher, 4.4 mmol/L or higher or 5.0 mmol/L or higher. In some embodiments, a method comprises supplementing, increasing, or elevating an amount or level of glucose in the central nervous system of a subject from a level below about 1.5 mmol/L, below about 1.8 mmol/L, below about 2.0 mmol/L, below about 2.2 mmol/L, or below about 2.5 mmol/L, to a level in a range of about 2 mmol/L to 50 mmol/L, 2.2 mmol/L to 50 mmol/L, 2.5 mmol/L to 50 mmol/L, 3 mmol/L to 50 mmol/L, 3.5 mmol/L to 50 mmol/L, 4 mmol/L to 50 mmol/L, 4.4 mmol/L to 50 mmol/L or 5.0 mmol/L to 50 mmol/L. In some embodiments, a method comprises supplementing, increasing, or elevating an amount or level of glucose in the central nervous system of a subject from a level below about 1.5 mmol/L, below about 1.8 mmol/L, below about 2.0 mmol/L, below about 2.2 mmol/L, or below about 2.5 mmol/L, to a level in a range of about 2 mmol/L to 10 mmol/L, 2.2 mmol/L to 10 mmol/L, 2.5 mmol/L to 10 mmol/L, 3 mmol/L to 10 mmol/L, 3.5 mmol/L to 10 mmol/L, 4 mmol/L to 10 mmol/L, 4.4 mmol/L to 10 mmol/L or 5.0 mmol/L to 10 mmol/L.

In certain embodiments, prior to administering a composition disclosed herein to a subject, a concentration of glucose in the central nervous system (e.g., in the brain, or CSF), is less than about 70, 65, 60, 55, 50, 45, 40, 35, 30, 25, 20, 15, or 10 mg/dL. In certain embodiments, prior to administering a composition disclosed herein to a subject, a concentration of glucose in the central nervous system of the subject (e.g., in the brain, or CSF), is from 5 to 70 mg/dL, from 5 to 60 mg/dL, from 5 to 50 mg/dL, from 5 to 40 mg/dL, from 5 to 30 mg/dL, from 5 to 20 mg/dL, from 5 to 10 mg/dL, from 10 to 70 mg/dL, from 10 to 60 mg/dL, from 10 to 50 mg/dL, from 10 to 40 mg/dL, from 10 to 30 mg/dL, from 10 to 20 mg/dL, from 20 to 70 mg/dL, from 20 to 60 mg/dL, from 20 to 50 mg/dL, from 20 to 40 mg/dL, from 20 to 30 mg/dL, from 30 to 70 mg/dL, from 30 to 60 mg/dL, from 30 to 50 mg/dL, or from 30 to 40 mg/dL. Such initial glucose level in a subject may vary depending upon a subject's physical or health condition, age, height, weight, sex, ethnicity, family medical history, as well as environmental factors, such as smoking habit and living conditions.

In certain embodiments, after the administration of a composition disclosed herein to a subject, a level of glucose in the central nervous system of the subject (e.g., in the brain, or CSF), is increased by at least 1%, 2%, 5%, 10%, 20%, 30%, 40%, 50%, 60%, 70%, 80%, 90%, 100%, 110%, 120%, 130%, 140%, 50%, 160%, 170%, 180%, 190%, 200%, 210%, 220%, 230%, 240%, 250%, 260%, 270%, 280%, 290%, or 300% compared to a level of glucose in the central nervous system of the subject prior to administration. In certain embodiments, after the administration of a composition disclosed herein to a subject, a level of glucose in the central nervous system of the subject (e.g., in the brain, or CSF), is increased by about 1 to 500%, about 1 to 200%, about 1 to 100%, about 1 to 50%, about 2 to 500%, about 2 to 200%, about 2 to 100%, about 2 to 50%, about 5 to 500%, about 5 to 200%, about 5 to 100%, about 5 to 50%, about 10 to 500%, about 10 to 200%, about 10 to 100%, or about 10 to 50% compared to a level of glucose in the central nervous system of the subject prior to administration. The percentage increase will vary from subject to subject and will depend upon the subject's physical or health condition, age, height, weight, sex, ethnicity, the nature and extent of the condition being treated, and recommendations of the treating physician.

In some embodiments, a method described herein comprises administering a composition disclosed herein as nutritional supplements as a means of increasing glucose concentrations in the central nervous system of a subject. A nutritional supplement or a supplement, in some embodiments, refers to a non-food form of L-serine administration. An non-limiting example of a supplement is a pharmaceutical preparation (such as chewable dosage form, a beverage formulation, a tablet, a capsule, a soft gel, a powder, a gel cap, a liquid, or a parenteral solution or other form).

L-Serine, or a Salt, a Precursor, Derivative or Conjugate Thereof

Provided herein are compositions comprising, or consisting essentially of L-serine, free L-serine, or a salt, a precursor, derivative or conjugate thereof, and uses thereof. In some embodiments, a composition consisting essentially of L-serine, free L-serine, or a salt, a precursor, a derivative or a conjugate thereof, comprises L-serine, free L-serine, or a salt, a precursor, a derivative or a conjugate thereof as the only active ingredient in the composition. Accordingly, a composition consisting essentially of L-serine, free L-serine, or a salt, a precursor, a derivative or a conjugate thereof may include various pharmaceutical excipients, additives, carriers and/or diluents. In some embodiments, a composition consisting essentially of L-serine, free L-serine, or a salt, a precursor, a derivative or a conjugate thereof excludes proteins or protein fractions comprising less than 100%, 99%, 98%, less than 95%, less than 90%, less than 80%, less than 70%, less than 60%, or less than 50% L-serine (wt/wt). In some embodiments, a composition consisting essentially of L-serine, free L-serine, or a salt, a precursor, a derivative or a conjugate thereof excludes proteins or protein fractions comprising greater than 20%, greater than 30%, greater than 40%, greater than 50% or greater than 60% protein (wt/wt). In some embodiments, a composition consisting essentially of L-serine comprises only free L-serine, or a polymer of L-serine having an amino acid content of L-serine of at least 100%, 99%, 98%, 95%, 90%, 85% or at least 80%, as the only active ingredient in the composition. In some embodiments, a composition consisting essentially of L-serine excludes creatine, creatine pyruvate, guanidino-acetic acid (GA), glycocyamine, N-amidinoglycine, and salts or esters thereof. In some embodiments, a composition consisting essentially of L-serine is a composition comprising free L-serine at a purity of at least 85%, at least 90%, at least 95%, at least 98%, at least 99% or 100%.

In some embodiments, a composition comprises free-L-serine. Free L-serine refers to L-serine in the form of a single amino acid monomer, or a salt thereof. In some embodiments, a composition comprises free L-serine at a purity of at least 85%, at least 90%, at least 95%, at least 98%, at least 99% or 100%. In certain embodiments, free L-serine is not covalently bonded to any other amino acid.

In some embodiments, a composition may exclude other active ingredients. In some embodiments, a composition may exclude proteins containing L-serine. In some embodiments, a composition may exclude proteins having a molecular weight greater than 10 kDa, greater than 20 kDa, greater than 30 kDa or greater than 50 kDa. In some embodiments, a composition may exclude proteins containing less than 99%, 98%, 95%, 92%, 90%, 80%, 70%, 60%, or less than 50% L-serine. In some embodiments, a composition may exclude creatine, or any energy metabolism precursor of creatine, such as guanidino-acetic acid (GA), equivalents thereof, and mixtures thereof.

In certain embodiments, a composition comprises L-serine, non-limiting examples of which include free L-serine, and polymers or polypeptides comprising at least a 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% L-serine by weight or amino acid content. In some embodiments, a polymer of L-serine or a polypeptide comprising L-serine includes between 2 and 50000, between 2 and 500, between 2 and 100, between 2 and 50, between 2 and 20, between 2 and 15, between 2 and 10, between 2 and 9, between 2 and 8, between 2 and 7, between 2 and 6, between 2 and 5, or between 2 and 4 L-serine amino acids linked by covalent bonds. In certain embodiments, a composition comprises L-serine, non-limiting examples of which include a polymer or polypeptide comprising from 20% to 100%, from 30% to 100%, from 35% to 100%, from 40% to 100%, from 45% to 100%, from 50% to 100%, from 55% to 100%, from 60% to 100%, from 65% to 100%, from 70% to 100%, from 75% to 100%, from 80% to 100%, from 85% to 100%, from 90% to 100%, from 95% to 100%, from 96% to 100%, from 97% to 100%, from 98% to 100%, or from 99% to 100% content of L-serine (wt/wt) or amino acid content (i.e., L-serine monomers/total amino acid monomers).

In some embodiments, a composition comprises a suitable derivative of L-serine. In certain embodiments, a composition comprises a salt of L-serine, non-limiting examples of which include a sodium salt, potassium salt, calcium salt, magnesium salt, zinc salt, ammonium salt; inorganic salts such as, hydrogen chloride, sodium chloride, potassium chloride, calcium chloride, sodium phosphate, potassium phosphate, and sodium hydrogen carbonate; organic salts such as, sodium citrate, citrate, acetate, and the like. In certain embodiments, a composition comprises L-serine as an alkylated L-serine, such as L-serine with an alkyl group, or e.g., an alkyl comprising 1-20 carbon atoms. In certain embodiments, a derivative of L-serine includes an L-serine ester, an L-serine di-ester, a phosphate ester of L-serine, or a sulfate or sulfonate ester of L-serine. Non-limiting examples of a conjugate of L-serine includes a pegylated L-serine (e.g., an L-serine comprising one or more polyethylene glycol (PEG) moieties), and a lipidated L-serine. Non-limiting example of a precursor of L-serine include L-phosphoserine.

In certain embodiments, a composition comprises a precursor of L-serine, non-limiting examples of which include a pro-form of L-serine that is broken down into L-serine monomers by the digestive system of a subject. In some embodiments, L-serine or a conjugate thereof consists of a slow-release version. In some embodiments a derivative of L-serine is conjugated to a different molecule forming a prodrug from which L-serine is released after crossing the blood/brain barrier.

L-serine is considered a nonessential amino acid because it is synthesized within astrocytes from glucose with PHGDH as a key enzymatic catalyst, but vertebrates cannot always synthesize it in sufficient quantities to meet necessary cellular demands. The biosynthesis of L-serine within the central nervous system begins with glucose which is converted to 3 phosphoglycerate. The 3 phosphoglycerate is in turn converted to phosphohydroxypyruvate through the enzyme 3-phosphoglycerate dehydrogenase. Phosphohydroxypyruvate is then converted to 3-phosphoserine through the enzyme phosphohydroxypyruvate aminotransferase. The 3-phosphoserine is converted to L serine through the enzyme phosphoserine phosphatase (de Koning et al., 2003). The conversion of glucose through this three enzyme system to L-serine is one of the many ways that glucose is used within the brain.

Although the three enzyme conversion system of glucose to L-serine has been considered unidirectional in nature, it may be possible to drive this biosynthetic pathway backwards through significant doses of L-serine. Specifically, through administration of high doses of L-serine administrated orally, through intramuscular or IV injection, or through direct infusion in the central nervous system, it is possible to convert L-serine to glucose through the PHGDH pathway.

Amino acids can be present in D or L stereoisomeric forms (enantiomers). The and L form of any amino acid have identical physical properties and chemical reactivities, but rotate the plane of plane-polarized light equally, but in opposite directions, and react at different rates with asymmetric reagents. Only the L-enantiomer occurs in human proteins; however, the D-enantiomer, in small quantities, is necessary as a cofactor at glutamate receptors for neurotransmission (Wolosker et al. 1999). As an unbranched naturally-occurring amino acid, L-serine is one of twenty amino acids that is used as a building block of proteins. The molar mass is 105.09 grams/mole. Since it is polar, it is soluble in water. A composition disclosed herein may comprise L-serine, or consist essentially of L-serine. A composition consisting essentially of L-serine may comprise some amount of D-serine. For example, a composition of the present disclosure may include a small amount of D-serine, for example, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, or less than 0.1% D-serine by weight (e.g., wt/wt) or amino acid content (e.g., L-serine/total amino acid content). For example, a composition may include from 0.001% to 30%, from 0.005% to 30%, from 0.1% to 30%, from 1% to 30%, from 2% to 30%, from 3% to 30%, from 4% to 30%, from 5% to 30%, from 6% to 30%, from 7% to 30%, from 8% to 30%, from 9% to 30%, from 10% to 30%, from 0.001% to 20%, from 0.005% to 0%, from 0.1% to 20%, from 1% to 20%, from 2% to 20%, from 3% to 20%, from 4% to 20%, from 5% to 20%, from 6% to 20%, from 7% to 20%, from 8% to 20%, from 9% to 20%, or from 10% to 20% D-serine. In some embodiments, a composition comprising or consisting essentially of L-serine, does not contain D-serine.

L-serine residues in neuroproteins are important sites for phosphorylation, allowing proper protein folding and functioning. As people age, concentrations of L-serine measured in blood and cerebral spinal fluid (CSF) can decrease. Even though some L-serine is synthesized endogenously within astrocytes and glial cells (de Koning and Klomp 2004), such age-related declines in L-serine concentrations indicate that L-serine dietary inputs may be necessary through life (van der Crabben et al. 2013). Dietary L-serine can be transported across the blood-brain barrier through the sodium dependent transporter and the alanine-serine-cysteine transporters asc-1 and asc-2 (Kasai et al. 2011). The therapeutic potential of L-serine was recently reviewed by Metcalf et al. (2017).

Dietary sources rich in L-serine include soy products, eggs, meat, seaweeds, and sweet potatoes. Within the body, L-serine can be recycled as other proteins are disassembled in lysosomes (de Koning et al. 2003, Kalhan and Hanson 2012). In cell culture, L-serine is necessary for cell proliferation (Yang and Vousden 2016). L-serine, which has been approved by the FDA as a GRAS (generally regarded as safe) food additive (CFR Title 21 Section 17.320.18), is sold by a variety of vendors as a health food supplement (Metcalf et al. 2017).

Recent ethnobotanical analyses of elderly populations, including centenarians, in Ogimi village, Okinawa, Japan suggested that dietary considerations may contribute to the absence of Alzheimer's disease or profound cognitive deficits in post-menopausal women in Ogimi (Cox and Metcalf, 2017). Elderly women of Ogimi not only are relatively devoid of motor neuron deficits and cognitive deficits including dementia, but appear to have nearly complete recall of their own lives back to the earliest portions of their childhood. These women are also extremely alert and responsive in interview situations.

The Ogimi villagers consume a diet based largely on tofu, edamame, pork, and a variety of wild harvested seaweeds, all of which are rich in L-serine (Cox and Metcalf, 2017). Sources of L-serine in the brain include endogenous biosynthesis within neurons and glial cells, as well as dietary L-serine which has been transported across the blood-brain barrier on the sodium dependent and sodium independent alanine-serine-cysteine transporters. A National Academy of Sciences survey found that the average American consumes 3.5 g/day from all dietary sources. In contrast, Ogimi villagers ingest 10-12 g/day from traditional food items (Cox and Metcalf, 2017).

Subjects

The term "subject" refers to a mammalian animal. Any suitable mammal can be treated by a method described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In certain embodiments a mammal is a human. A mammal can be any age or at any stage of development (e.g., an adult, teen, child, or infant). In certain embodiments, a subject is a human in the age range of 1 year and 55 years, 1 year and 50 years, 1 year and 45 years, 1 year and 40 years, 1 year to 21 years, or over the age of 50. In certain embodiments, a subject is a man over the age of 50. In certain embodiments, a subject is a post-menopausal woman. In certain embodiments, a subject is a woman over the age of 50. A mammal can be male or female. In certain embodiments, a subject is human in need of a treatment method disclosed herein. In certain embodiments, a subject is a human having, or suspected of having one or more of the diseases or conditions disclosed herein.

In certain embodiments, a subject is not diabetic, and/or is not know to have diabetes. In certain embodiments, a subject does not have Type I or Type II diabetes. In certain embodiments, a subject does not have Alzheimer's disease (AD), and/or is not know to have AD. In certain embodiments, a subject does not have ALS, AD, ALS\PDC, dementia, PD, HD, PSP, or LBD, and/or is not know to have ALS, AD, ALS\PDC, dementia, PD, HD, PSP, or LBD. In certain embodiments, a subject has, or is at risk for developing one or more diseases or conditions associated with decreased GLUT1 and/or GLUT3 levels. In certain embodiments, a subject can be identified as having, or at risk of developing cognitive impairment.

Dose and Therapeutically Effective Amount

Methods and uses of the present disclosure include administering L-serine, or a salt, precursor, derivative, or conjugate thereof, to a subject at a dose disclosed herein or at a dose intended to achieve a therapeutic effect (e.g., a therapeutically effective amount). In some embodiments, an amount of L-serine for use in a method described herein is a therapeutically effective amount. In certain embodiments, a composition (e.g., a pharmaceutical composition) comprises a therapeutically effective amount of a L-serine, a conjugate, salt, derivative or precursor thereof. In some embodiments, a therapeutically effective amount of L-serine, a conjugate, salt, derivative or precursor thereof is administered to a subject. In some embodiments, a therapeutically effective amount of a compound for use in a method described herein is an amount needed to obtain an effective therapeutic outcome. In certain embodiments, a therapeutically effective amount of a compound for use in a method described herein is an amount sufficient to increasing or regulate glucose concentration in the central nervous system of a subject, inhibit or delay cognitive decline in a subject, enhance cognitive function in a subject, enhance memory or learning ability in a subject, and/or to treat a disease or condition associated with a decreased level of glucose in the central nervous system of a subject. Determination of an effective amount or a therapeutically effective amount is well within the capability of those skilled in the art, especially in light of the detailed disclosure provided herein.

In certain embodiments, a therapeutically effective amount is an amount high enough to provide an effective therapeutic effect (e.g., a beneficial therapeutic effect) and an amount low enough to minimize unwanted adverse reactions. Accordingly, in certain embodiments, a therapeutically effective amount of L-serine for use in a method described herein may vary from subject to subject, often depending on age, weight, general health condition of a subject. Thus, in some embodiments, a therapeutically effective amount is determined empirically. Accordingly, a therapeutically effective amount of a compound for use in a method described herein that is administered to a subject can be determined by one of ordinary skill in the art based on amounts found effective in animal or clinical studies, a physician's experience, and suggested dose ranges or dosing guidelines, for example. In certain embodiments, a therapeutic effect is an achievement of the desired and/or beneficial consequences of a treatment according to the methods herein. Such desirable and/or beneficial results include, but are not limited to, (i) an increase in glucose concentration in the central nervous system of a subject, (ii) a prevention, inhibition, or delay of the reduction of glucose concentration in the central nervous system of a subject, (iii) an inhibition, prevention, suppression, decrease, or delay in cognitive decline of a subject, (iv) cognitive enhancement, or (vi) prevention or treatment of a disease or condition disclosed herein.

In certain embodiments, a therapeutically effective amount is an amount of a composition disclosed herein, administered at dosages and/or for periods of time necessary to achieve the above mentioned desired and/or beneficial consequences of a method disclosed herein. In certain embodiments, a therapeutically effective amount is an amount sufficient to improve short-term memory (working memory), long-term memory, processing speed, mental alertness, mental concentration, attention span, learning ability, reaction time, mental clarity, mental energy, or general reasoning in a subject. In some embodiments, a therapeutically effective amount is determined empirically.

In certain embodiments, a therapeutically effective amount of a composition disclosed herein is administered at a suitable dose (e.g., at a suitable volume, frequency and/or concentration, which often depends on a subject's weight, age and/or condition) intended to obtain an acceptable therapeutic outcome. In certain embodiments, a therapeutically effective amount of a composition disclosed herein comprises one or more doses (administered to a subject) selected from at least 0.1 mg/kg (e.g., mg of a compound herein per kg body weight of a subject), at least 5 mg/kg, at least 10 mg/kg, at least 15 mg/kg, at least 20 mg/kg, at least 25 mg/kg, at least 50 mg/kg, at least 100 mg/kg, at least 250 mg/kg, at least 500 mg/kg, at least 1000 mg/kg, at least 5000 mg/kg, or at least 7500 mg/kg. In certain embodiments, a therapeutically effective amount of a composition disclosed herein comprises administering one or more doses (administered to a subject) of about 1 mg/kg/day (e.g., mg of a composition disclosed herein per kg body weight of a subject per day) to about 7500 mg/kg/day, for example, 10 to 7500 mg/kg/day, 50 to 7500 mg/kg/day, 100 to 7500 mg/kg/day, 250 to 7500 mg/kg/day, 428 to 7500 mg/kg/day, 500 to 7500 mg/kg/day, 1000 to 7500 mg/kg/day, 1001 to 7500 mg/kg/day, 1500 to 7500 mg/kg/day, intervening amounts and combinations thereof.

In certain embodiments, a therapeutically effective amount of a composition disclosed herein comprises one or more doses (administered to a subject) of at least 100 mg, 500 mg, 1 g, 5 g, 10 g, 20 g, 30 g, 40 g, 50 g, 60 g, 70 g, 71 g, or at least 80 g. In certain embodiments, a therapeutically effective amount of a composition disclosed herein comprises one or more doses (administered to a subject) of about 0.5-200 g, 1-100 g, 1-90 g, 1-80 g, 1-70 g, 1-60 g, 1-30 g, 1-25 g, 10-100 g, 20-100 g, or 71-200 g.

In some embodiments administering a therapeutically effective amount of a composition disclosed herein comprises administering a suitable dose hourly, every two hours, every 4 hours, every 6 hours, every 8 hours, or every 12 hours. In certain embodiments, the composition disclosed herein can be administered at least one, at least two, at least three, at least four, at least five times, or at least six times per day, e.g., 1 to 12 times per day, 1 to 8 times per day, or 1 to 4 times per day per day, or administered once, twice, 3 times, 4 times, 5 times, 6 times, 7 times, 8 times, 9 times, 10 times, 11 times, or 12 times per day. The composition may be administered in a single dosage form or one or more dosage forms. The daily dose can be achieved in the form of a single dose or in the form of a plurality of partial doses.

A composition disclosed herein can be administered on a daily basis or on a schedule containing days where dosing does not take place. For example, dosing may take place every other day, or dosing may take place for 2, 3, 4, or 5 consecutive days of a week, then be followed by from 1 to 5 non-dosing days.

A composition herein can be administered for at least a day, at least two days, at least three days, at least four days, at least five days, at least a week, at least two weeks, at least three weeks, at least a month, at least two months, at least three months, at least four months, at least five months, at least six months, at least a year, at least two years, or more, or for any extended duration to further improve, maintain, or retain improved cognition. In particular embodiments, the level of cognitive ability of the subject taking the composition may play a role in determining the length of use. In certain embodiments, a composition herein can be administered for a duration of from 1 day to 36 months, which includes 2 days, 3 days, 4 days, and so forth, as well as 1 week, 2 weeks, 3 weeks, 4 weeks, and so forth, as well as 1 months, 2 months, 3 months, 4 months, and so forth, and combinations thereof, non-limiting example such as, 2 months and 3 weeks and 4 days, etc. In certain embodiments, the duration is from 1 week to 24 weeks, from 2 weeks to 24 weeks, from 3 weeks to 24 weeks, from 4 weeks to 24 weeks, from 5 weeks to 24 weeks, from 1 week to 12 weeks, from 2 weeks to 12 weeks, from 3 weeks to 12 weeks, from 4 weeks to 12 weeks, from 5 weeks to 12 weeks.

Route of Administration

Any suitable method of administering a composition, pharmaceutical composition or L-serine for use in a method described herein to a subject can be used. Any suitable formulation and/or route of administration can be used for administration of a composition, pharmaceutical composition or L-serine for use in a method described herein (e.g., see Fingl et al. 1975, in "The Pharmacological Basis of Therapeutics", which is incorporated herein by reference in its entirety). A suitable formulation and/or route of administration can be chosen by a medical professional (e.g., a physician) in view of, for example, a subject's risk, age, and/or condition. Non-limiting examples of routes of administration include topical or local (e.g., transdermally or cutaneously, (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranial, intra-articular, into a joint space, intracardiac (into the heart), intracavernous injection, intralesional (into a skin lesion), intraosseous infusion (into the bone marrow), intrathecal (into the spinal canal), intrauterine, intravaginal, intravesical infusion, intravitreal), the like or combinations thereof. In some embodiments, a composition disclosed herein is administered orally.

Compositions

Compositions disclosed herein can be administered in various forms or formulations. For example, where the compositions are to be administered orally, they may be formulated as powders, chewable dosage forms, beverage formulations, tablets, capsules, soft gels, gel caps, or liquids; or for parenteral administration, they may be formulated as injections (intravenous, intramuscular, or subcutaneous). In some embodiments, a composition disclosed herein is formulated as a powder or granules suitable for dissolving in an aqueous, ingestible solvent (e.g., water, coffee, juice, wine, beer, a sports drink, an energy drink, a nutrient drink, and the like).

Compositions suitable for or a administration may be presented as discrete units such as capsules, cachets, or tablets, soft gels, gel caps, chewable dosage units (e.g., chewable tablets, quick chew, gummy, lozenges, health bars, foods, cereal coatings, food supplements, nutritional supplements), each containing a therapeutically effective amount of the composition, as a powder or granules, or as a solution or a suspension in an aqueous liquid, a non-aqueous liquid, an oil-in-water emulsion, or a water-in-oil liquid emulsion. In general; the compositions are prepared by homogenously admixing the active ingredients with liquid carriers or finely divided solid carriers or both, and then, if necessary, shaping the product into the desired presentation. In some embodiments a composition suitable for oral administration comprises a slow-release version of L-serine. In some embodiments, a slow-release version of L-serine comprises a conjugate of L-serine. In some embodiments, L-serine is conjugated to a different molecule forming a prodrug from which L-serine is released after crossing the blood/brain barrier.

The compositions can additionally include inactive ingredients such as binding agents (such as pregelatinized maize starch, polyvinylpyrrolidone or hydroxypropyl methylcellulose); binders or fillers (such as lactose, pentosan, microcrystalline cellulose or calcium hydrogen phosphate); lubricants (such as magnesium stearate, talc or silica); disintegrants (such as potato starch or sodium starch glycolate); or wetting agents (such as sodium lauryl sulphate). The composition can include magnesium stearate, The composition, such as the tablet, can include pharmaceutically acceptable ingredients, such as lactose, glucose, sucrose, corn starch, potato starch, cellulose esters such as cellulose acetate, ethyl cellulose, magnesium stearate, calcium silicate, precipitated silica, talc, fatty acids such as stearic acid, microcrystalline cellulose, carnauba wax and the like. The tablets or capsules can be coated by methods well known in the art.

In certain embodiments, the chewable dosage forms may include any necessary additive required to achieve a chewable structure.

Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives that are inactive agents, such as suspending agents (such as sorbitol syrup, cellulose derivatives or hydrogenated edible fats), emulsifying agents (such as lecithin or acacia), nonaqueous vehicles (such as almond oil, oily esters, ethyl alcohol or fractionated vegetable oils), and preservatives (such as methyl or propyl-p-hydroxybenzoates or sorbic acid). The compositions can also be made to be pleasant tasting, and thus can contain buffer salts, flavoring, coloring and sweetening agents as appropriate.

In certain embodiments, the composition may be formulated in a beverage that, in some embodiments, is provided in a suitable container (e.g., a can, bottle or carton) and/or in a concentrated or ready-to-drink formulation suitable for human consumption. In some embodiments, a beverage is prepared by mixing the composition disclosed herein in power form with a non-alcoholic beverage, such as water, milk, any flavored beverages, soda, to provide a beverage formulation in which the composition (in powder form) is dispensed. In one embodiment, the beverage is prepared by mixing the composition disclosed herein in liquid form with a non-alcoholic beverage to provide a beverage formulation in which the composition (in liquid form) is dispensed.

The unit dose forms may be individually wrapped, packaged as multiple units, or in bottles, or vials of any size, without limitation.

For parenteral administration, intravenous injection, subcutaneous injection, muscle injection, intraperitoneal injection, endothelial administration, topical administration, intranasal administration, and the like may be performed. Parenteral solutions containing L-serine may be prepared under sterilized conditions usually in a 1 to 30% concentration dissolved in, or in fine suspension in a pharmaceutically acceptable vehicle.

In some embodiments, a composition or a pharmaceutical composition disclosed herein is provided to a subject. For example, a composition that is provided to a subject is sometimes provided to a subject for self-administration or for administration to a subject by another (e.g., a non-medical professional). As another example, a composition can be provided as an instruction written by a medical practitioner that authorizes a patient to be provided a composition or treatment described herein (e.g., a prescription). In yet another example, a composition can be provided to a subject where the subject self-administers a composition orally, or intravenously, for example.

Pharmaceutical compositions comprising L-serine, or a precursor, derivative or conjugate thereof, as described herein can be formulated in any suitable manner using one or more pharmaceutically acceptable carriers, non-limiting examples of which include carriers, solvents, salts, excipients, additives, preservatives, and/or auxiliaries. Proper formulation can depend upon the route of administration chosen. In particular, a pharmaceutical compositions can comprise any suitable carrier, formulation, or ingredient, the like or combinations thereof as listed in "Remington: The Science And Practice Of Pharmacy" Mack Publishing Co., Easton, PA, 19th Edition, (1995), or "Remington: The Science And Practice Of Pharmacy", Pharmaceutical Press, Easton, PA, 22$^{nd}$ Edition, (2013). The various materials listed herein, alone or in combination, can be incorporated into or used with the materials described in Remington's. Any suitable techniques, carriers, and excipients can be used, including those understood in the art; e.g., in Remington's Pharmaceutical Sciences, above.

In some embodiments, a compositions comprising, or consisting essentially of, L-serine, or a precursor, derivative or conjugate thereof, as described herein, is formulated for oral administration as a slow release, or sustained release preparation. In some embodiments, a compositions comprising, or consisting essentially of, L-serine, or a precursor, derivative or conjugate thereof, as described herein, is a slow release or sustained release composition. Any suitable method of preparing a slow release or sustained release composition can be used. In some embodiments, a sustained release formulation comprises a gelling agent; at least one inert pharmaceutical diluent selected from the group consisting of monosaccharides, disaccharides, polyhydric alcohols, and mixtures thereof; and a pharmaceutically acceptable cationic cross-linking agent capable of crosslinking with the gelling agent.

In certain embodiments, a method comprises increasing or regulating glucose concentration in the central nervous system of a subject comprising administering to the subject a composition comprising a therapeutically effective amount of between 10 and 100 g of L-serine, or a precursor or conjugate thereof. In certain embodiments, a method comprises treating a disease or condition associated with a decreased level of glucose in the central nervous system of a subject, wherein said disease or condition is GLUT1 deficiency syndrome, comprising administering to the subject a composition comprising a therapeutically effective amount of between 10 and 100 g of L-serine, or a precursor or conjugate thereof. In certain embodiments, a method comprises inhibiting or delaying cognitive decline in a subject comprising administering to the subject a composition comprising a therapeutically effective amount of between 10 and 100 g of L-serine, or a precursor or conjugate thereof. In certain embodiments, a method comprises enhancing cognitive function, memory or learning in a subject comprising administering to the subject a composition comprising a therapeutically effective amount of between 10 and 100 g of L-serine, or a precursor or conjugate thereof. In further embodiments, the subject suffers from GLUT1 deficiency syndrome, MCI, AMCI, AAMI, ARCD, chemotherapy-induced cognitive dysfunction, or ADHD. In some embodiments, the subject is hypoglycemia. In some embodiments, the subject is diabetic. In some embodiments, the subject is a post-menopausal woman.

EXAMPLES

A number of embodiments of the disclosure have been described. Nevertheless, one skilled in the art, without departing from the spirit and scope of the disclosure, can make various changes and modifications of the disclosure to adapt it to various usages and conditions. Accordingly, the following examples are intended to illustrate, but not limit, the scope of the disclosure claimed in any way. The following Examples serve as an illustration of embodiments disclosed herein. Amounts of L-serine expressed in the examples herein refer to amounts of the free form of L-serine, unless indicated otherwise.

Example I

This Example describes experimental confirmation of the utility of L-serine in increasing glucose concentrations within the CNS.

One way of substantiating the utility of L-serine therapy or treatment of glucose deficiency syndrome can be found through observations of increased glucose and lactate in cerebral spinal fluid (CSF) samples taken from nonhuman primates, in this case four vervets (Chlorocebus pygerythrus), which were fed daily doses of 651 mg/day of L serine for 42 days. These were compared to four control vervets who were fed daily control doses of 651 mg/day of rice powder for 42 days.

Cerebral spinal fluid samples were taken during the experiment. The cerebral spinal fluid samples from vervets fed L-serine were compared to cerebral spinal fluid samples from control vervets at 42 days.

Frozen cerebral spinal fluid (CSF) was prepared using equal volumes of CSF and 20% w/v TCA. The combined volume was sonicated (Fisher Scientific Sonic Dismembrator, Model 100) on ice at 2 watts (10 s×3) and left to precipitate at room temperature for 30 minutes. The sample was then centrifuged (Labnet Spectrafuge 16M) at 14,000 g for 5 min. The supernatant was filtered with a centrifuge filter (0.2 μm, Millipore UltrafreeMC) at 14,000×g for 5 min. Samples were diluted 1:3 with 50% CH3CN in purified water (18MΩ Millipore) before analysis.

CSF extracts were analyzed on a TSQ Quantiva (Thermo Scientific) triple quadrupole mass spectrometer with an Ultra High Pressure Liquid Chromatography (Waters Acquity-UHPLC) system equipped with a Binary Solvent Manager, Sample Manager, and an Acquity UPLC BEH Amide column (#186004801, 100×2.1 mm, 1.7 μm) at 50° C. Mobile phase A was 70:30 18MΩ purified water (Millipore): CH3CN with 0.1% NH4OH and mobile phase B was 20:80 18MΩ purified water (Millipore): CH3CN with 0.1% NH4OH. Seal wash was 90:10 18MΩ purified water (Millipore): methanol and strong needle wash and weak needle wash were both 5:95 18MΩ purified water (Milipore): CH3CN. Separation was achieved using a linear gradient from 20% to 50% A over 5 min followed by a column wash and column equilibration. Using this gradient fructose and sucrose were separated from glucose by more than 6 sec.

The mass spectrometer was operated with a heated electrospray ionization (H-ESI) probe and sheath gas pressure set to 40 (Arb), aux gas set to 2 (Arb), and sweep gas set to 1 (Arb). Samples were analyzed in negative ion mode with a vaporizer temperature of 350° C., capillary temperature of 130° C., and spray voltage 2800v. Scan width was set to 10 Da and dwell time was 40 ms. Single ion monitoring was used to monitor two ions (m/z 179 and 341). Glucose concentrations were linear over six concentration of 1:2 dilutions from 0.0098 to 0.039 mg/ml with 5 ul injections (f(x)=9.7367e-11x–2.12e-4; R2=0.97).

The median glucose levels in control vervet brains s were 24 mg/100 ml of CSF. In the vervets fed L-serine, the median level of glucose in their brains was 58 mg/100 ml.

The chi-square statistic was 23.125, indicating that this increase, a great than doubling of glucose levels, is significant at the p<0.005 level.

This demonstrates that it is possible to more than double the amount of glucose in the central nervous system through oral dosing of L-serine and confirms that it is possible to reverse the biosynthetic pathway of L-serine within astrocytes and glial cells through significant doses of L-serine.

Thus, it is possible to increase glucose concentrations within the CNS without recourse to the typical glucose transporter proteins, including GLUT1, GLUT3, SGLT1, SGLT2. Accordingly, it is possible to build a bridge for glucose across the blood brain barrier in the case of defective glucose transporters by utilizing amino acid transporters with L-serine as a precursor.

Example 2

This Example demonstrates that human neuroblastoma cells (SH-SY5Y) do not synthesise glucose when provided with L-serine.

The unique ability of astrocytes, glia, and neurons to transform L-serine into glucose by means of reversing the pathway described above is supported by studies of human neuroblastoma cells (SH-SY5Y) which conclusively show that they cannot transform L-serine into glucose.

Cell Culture: SH-SY5Y human neuroblastoma (PD19, ATCC® CRL-2266™) were cultured in 150 cm² flasks in Dulbecco's Modified Eagle's Medium/Nutrient F-12 Ham (Sigma-Aldrich, Cat. No. D8437) containing 10% fetal bovine serum (FBS), 4 mM L-glutamine, 100 U/mL penicillin, and 100 μg/mL streptomycin at 37° C. (Complete Medium) in a humidified atmosphere of 5% $CO_2$ and 95% air. At between 70 and 90% confluence, the cells were trypsinized with 0.5% Trypsin-EDTA (Thermo Fisher, Cat. No. 15400054) and then $2.5 \times 10^5$ cells/well plated in twenty-four-well plates and allowed to adhere overnight (PD22).

The following day, the cell culture medium was aspirated, and the cells were washed three times in warm (3TC) Hanks buffered salt solution (HBSS). Cells were then starved in Starvation Medium (custom DMEM/Ham's F12 1:1 Mixture deficient in glucose, glycine, L-serine, sodium pyruvate and phenol red (Caisson Labs, Utah, USA, Lot 09181022) supplemented with 100 U/mL penicillin, and 100 μg/mL streptomycin) for 6 hrs. The starvation medium was removed and replaced with 500 μL treatment medium which was Starvation Medium supplemented with 100 mM L-serine, 200 mM L-serine or 500 mM L-serine, in triplicate. Cells grown in Complete Medium served as a positive control, and cells grown in custom DMEM/Ham's F12 1:1 Mixture deficient in glucose, glycine, L-serine, sodium pyruvate and phenol red, served as a negative control.

Preparation of Medium and Lysate Fractions:

For t=24 and 48 hrs, the cells were returned to the incubator. For t=0, the Treatment Medium was removed immediately and aliquoted into 1.5 mL Eppendorf tubes, which was spun at 2000×g for 5 mins at 4° C. To the attached cells, 500 μL 0.1% ice-cold Triton X-100 was added to each well and the plate was placed on a plate shaker for 10 mins. After centrifugation, the supernatant was removed and aliquoted into a fresh 1.5 mL Eppendorf tube. This fraction became "Medium". The lysates from the cells treated with Triton X-100 were combined with the pellets remaining from the centrifugation of the Medium fraction. This fraction then became "Lysates". This processing was repeated for t=24 and 48 hrs. Medium and Lysates were stored at −20° C. until needed for glucose analysis.

Glucose Quantitation:

Cell fractions (Medium and Lysates) were removed from the −20° C. and freeze-thawed three times, in a 37° C. water bath and −80° C. freezer, with vortexing in between. Glucose concentrations were measured using the Amplex® Red Glucose/Glucose Oxidase Assay Kit (Invitrogen). Briefly, a glucose standard curve, consisting of 7 serial dilutions from 200 μM, was prepared from 4 mM D-glucose prepared in 1× reaction buffer. 50 μL of each standard was aliquoted into a 96-well plate in triplicate. For samples, the positive control samples (Complete Medium) were diluted 10 times into 1× reaction buffer. All other samples were assayed neat, with 50 μl, in duplicate. 50 μL Amplex® Red reagent buffer was added to each well and the plate incubated for 30 mins, in the dark. Fluorescence was read at excitation 540 nm and emission 590 mm in SoftMax Pro version 7.0.2 on a Molecular Devices Flexstation 3. Glucose concentrations in the samples were calculated from the standard curve. Results for Medium are shown in FIG. 1.

The results shown in FIG. 1 demonstrate that human neuroblastoma cells do not synthesise glucose when provided with L-serine. Human neuroblastoma cells were incubated in medium deficient in glucose and L-serine, but supplemented with increasing concentrations of L-serine (100, 200 and 500 mM) for 0, 24 and 48 hrs, then glucose concentrations in the culture medium measured using the Amplex® Red Glucose Assay (Invitrogen). No significant increase in glucose concentrations in the culture medium was observed in any of the elevated L-serine concentrations compared to Control (i.e., 0 mM L-serine).

This data demonstrates it is not apparently obvious that the CNS can convert L-serine to glucose to provide the benefits disclosed herein.

Example 3

This Example describes a nutritional experiment conducted on post-menopausal women. The study was designed to determine if dietary supplementation with L-serine (15 grams/day) improves cognitive ability in healthy women when administered over a 60-day period. Forty-eight women ages 55 years, who had not been diagnosed with mild cognitive impairment, probable dementia, or Alzheimer's disease participated as volunteers in this randomized, placebo-controlled double-blinded study. Forty-three women completed the study. Cognitive abilities of each participant were assessed in several different cognitive domains by using the NIH toolbox (Gershon et al, 2013) on an I-Pad, founded on earlier test procedures developed by Atkinson and Shiffrin (1968). Cognitive tests included the Rey Auditory Verbal Learning Test which broadly assesses short-term auditory and verbal learning (King et al. 1998). For example, in one test participants were presented 15 unrelated words and asked to repeat them again after 30 minutes. The cognitive assessment was administered to participants at the beginning and the end of the sixty-day study period. The assessment procedure lasted 45 minutes for each individual.

Two lots of L-serine were used to manufacture the L-serine gummies prepared for the study. L-serine powder was independently screened during packaging and throughout the trial using triple quadruple liquid chromatography mass spectrometry. The lots analyzed met the necessary criteria as determined by triple quadruple mass spectrometry for use in human clinical trials and were spectroscopically consistent with an authenticated standard provided by Sigma-Aldrich (St. Louis, MO).

L-serine, as a small (105.09 MW) proteinogenic amino acid, proved extraordinarily stable when tested over a 24 month storage period when held at room temperature (<30° C.) at a relative humidity of <75%. No significant changes were observed in optical rotation or purity over this period.

L-serine gummies, each at 2.2 grams total weight, and each containing 1.0 grams of L-serine were manufactured in a cGMP FDA-compliant facility by Knechtel (Skokie, IL). Placebo gummies were manufactured in a similar manner. The placebo gummies were of the same size, shape, color, taste, and weight, but did not contain L-serine. The gummies were placed in sealed foil packets, each packet containing 15 gummies. Microbiological analysis indicated the gummies to be free of bacterial contamination. The materials used for packaging were manufactured by ESP Packaging LLC (Costa Mesa, CA).

Each individual foil packet was labeled with a lot number containing the Julian code date. A box containing multiple packets designated for the sixty-day study was delivered to each study participant with directions for one foil pack (15 gummies) to be consumed by the participant throughout each day.

Twenty-three women were given 60 foil packets containing placebo gummies, and twenty-five women were given 60 foil packets containing L-serine gummies. Accordingly, women who received the L-serine gummies were administered 15 grams/day of L-Serine for 60 days. At the end of the trial, for each participant, the beginning learning and memory scores were subtracted from the final learning and memory scores.

Two Alternative Hypotheses were Tested:

$H_0$: there is no difference between L-serine and placebo treatment groups in improvement on the Rey Auditory Verbal Learning Test, and $H_1$: the L-serine treatment group showed more improvement on the Rey Auditory Verbal Learning Test than the placebo treatment group.

The differences between the beginning and end score for each participant in the L-serine treatment and placebo treatment groups were evaluated using a Wilcoxon-Mann-Whitney test with $p<0.05$ as the significance level. The participants taking 15 g/day of L-serine had a mean improvement of 7.9 on the Rey Auditory Verbal Learning Test, while those assigned to the placebo group had a mean improvement of 4.0. Accordingly, women who received the L-serine gummies showed a significantly greater ($p<0.01$) improvement in learning ability, with a median score 98% higher as measured by the Rey Auditory Verbal Learning Test, compared to the placebo group. In addition, there was a trend towards improvement for the delayed list recall for the L-serine treatment, but this trend did not achieve statistical significance.

The Wilcoxon-Mann-Whitney test U statistic for the difference between treatment groups was 124.16 with a variance of 38.34, corresponding to a z statistic of 2.24. Thus, the null hypothesis was rejected at $p<0.01$.

It was found that dietary supplementation of L-serine at 15 g/day resulted in a 98% improvement in learning ability in the participants as measured by the Rey Auditory Verbal Learning Test. This result indicated that 15 g L-serine taken daily can improve cognitive ability and may explain the extraordinary recall of elderly women in Ogimi village who consumed 10-12 g L-serine per day in the tofu and various seaweeds that they gather.

Since L-serine is generally recognized as safe (GRAS) by the FDA, and there are no significant adverse events reported for its use as a dietary supplement. Therefore, it is unlikely that the use of L-serine to enhance cognition will result in the same problems that are associated with misuse of Adderall, Ritalin, Modanfinil, and other prescription drugs. A recent Phase I study of 20 ALS patients found L-serine to be safe at up to 30 g/day over a six-month period (Levine et al., 2017), and currently an FDA-approved Phase IIa study is assessing safety and tolerability of L-serine at 30 g/day for early stage Alzheimer's patients (ClinicalTrials.gov identifier NCT03062449). Based on the current study, it therefore appears that doses within the range of 10-15 g/day of L-serine may prove both safe and effective for cognitive enhancement (i.e., enhancing cognitive function) in healthy postmenopausal women.

Example 4

This Example describes the efficacy of treating glucose deficiency syndrome with L-serine.

Evidence for the efficacy of L-serine therapy for glucose deficiency syndrome is supported by a case-study of a 30-year-old man ("the patient") who suffered ataxia, developmental impairment, reduced social interaction, and fine motor skill deficits as a result of his GLUT1 deficiency. In subjects suffering from glucose deficiency syndrome, there is insufficient glucose transported across the brain to allow proper functioning of brain cells. Since L-serine is transported through a different mechanism across the blood brain barrier, it is possible to increase intracranial glucose concentrations through administration of high doses of L-serine. The patient was administered 30 grams of L-serine per day by oral administration. Within several weeks of beginning oral ingestion of high dose L-serine, the patient with GLUT1 deficiency demonstrated rapid improvement in his condition, including regaining the ability to ride a bicycle and to carry cargo while doing so. The patient also demonstrated improved social interaction, including the ability to look into people's eyes while speaking; improved fine motor skills, including handwriting; and general increased health and vigor.

These results suggested that increased glucose in the brain through dosing with L-serine may provide improvements in a variety of developmental, neurological, and psychiatric ailments characterized by, associated with, or caused by inadequate concentrations of glucose within the brain.

The results also suggest that healthy people may experience a significant increase in learning ability by taking daily doses of L-serine in the 5-30 gram/day dose range.

As indicated in this Example, a clinical case study involving a single patient, oral dosing with L-serine can result in a reduction of, lessening of, or elimination of, one or more symptoms caused by GLUT1 deficiency syndrome.

It is reasonable to extrapolate that dosing with L-serine, through a similar mechanism, may result in a measurable increase in cognitive ability in patients suffering from Alzheimer's disease, Parkinson's disease with dementia, ALS patients with dementia, Progressive Supranuclear Palsy (PSP), Lewy Body dementia, frontotemporal dementia, and other forms of cognitive impairment. Decreased glucose transporters are associated with hyperphosphorylation of tau in Alzheimer's disease (Liu et al., 2008). L-serine administration to experimental animals in which Alzheimer's-type neuropathology has been triggered should result in a significant quantitative decrease of hyperphosphorylated tau.

This mechanism of increasing intracranial glucose through utilizing L-serine transport across the blood brain barrier, may have other beneficial indications. If, for example, cognitive ability is limited by the amount of glucose available to the brain through glucose transporters, dosing with L-serine may improve cognitive ability by increasing glucose in the CNS.

REFERENCES

Atkinson R C, Shiffrin R M. Human memory: A proposed system and its control processes. Psychology of learning and motivation. 1968 Dec. 31; 2:89-195.

Cox P A, Metcalf J S. Traditional food items in Ogimi, Okinawa: L-serine content and the potential for neuroprotection. Current Nutrition Reports. 2017 Mar. 1; 6(1): 24-31.

de Koning T J, Klomp L W. Serine-deficiency syndromes. Current opinion in neurology. 2004 Apr. 1; 17(2):197-204.

de Koning T J, Snell K, Duran M, Berger R, Surtees R. L-serine in disease and development. Biochemical Journal. 2003 May 1; 371(3):653-61.

Duffy R, Wiseman H, File S E. Improved cognitive function in postmenopausal women after 12 weeks of consumption of a soya extract containing isoflavones. Pharmacology Biochemistry and Behavior. 2003 Jun. 30; 75(3):721-9.

Duka T, Tasker R, McGowan J F. The effects of 3-week estrogen hormone replacement on cognition in elderly healthy females. Psychopharmacology. 2000 Apr. 18; 149(2):129-39.

Gershon R C, Wagster M V, Hendrie H C, Fox N A, Cook K F, Nowinski C J. NIH toolbox for assessment of neurological and behavioral function. Neurology. 2013 Mar. 12; 80(11 Supplement 3):52-6.

Greely, H., Sahakian, B., Harris, J., Kessler, R. C., Gazzaniga, M., Campbell, P. and Farah, M. J., 2008. Towards responsible use of cognitive-enhancing drugs by the healthy. Nature, 456(7223), p. 702.

Hogervorst E, Williams J, Budge M, Riedel W, Jolles J. The nature of the effect of female gonadal hormone replacement therapy on cognitive function in post-menopausal women: a meta-analysis. Neuroscience. 2000 Nov. 15; 101(3):485-512.

Jacobs D M, Tang M X, Stern Y, Sano M, Marder K, Bell K L, Schofield P, Dooneief G, Gurland B, Mayeux R. Cognitive function in nondemented older women who took estrogen after menopause. Neurology. 1998 Feb. 1; 50(2):368-73.

Kalhan S C, Hanson R W. Resurgence of serine: an often neglected but indispensable amino Acid. Journal of Biological Chemistry. 2012 Jun. 8; 287(24):19786-91.

Kasai Y, Tachikawa M, Hirose S, Akanuma S I, Hosoya K I. Transport systems of serine at the brain barriers and in brain parenchymal cells. Journal of neurochemistry. 2011 Jul. 1; 118(2):304-13.

King J H, Gfeller J D, Davis H P. Detecting simulated memory impairment with the Rey Auditory Verbal Learning Test: Implications of base rates and study generalizability. Journal of clinical and experimental neuropsychology. 1998 Oct. 1; 20(5):603-12.

Ilieva, I., Boland, J. and Farah, M. J., 2013. Objective and subjective cognitive enhancing effects of mixed amphetamine salts in healthy people. Neuropharmacology, 64, pp. 496-505.

Levine T D, Miller R G, Bradley W G, Moore D H, Saperstein D S, Flynn L E, Katz J S, Forshew D A, Metcalf J S, Banack S A, Cox P A. Phase I clinical trial of safety of L-serine for ALS patients. Amyotrophic Lateral Sclerosis and Frontotemporal Degeneration. 2017 Jan. 2; 18(1-2):107-11.

Metcalf J S, Dunlop R A, Powell J T, Banack S A, Cox P A. L-serine, a naturally-occurring amino acid with therapeutic potential. Neurotoxicity Research 2017. Sep. 19:1-9

Sahakian, B. J., Bruhl, A. B., Cook, J., Killikelly, C., Savulich, G., Piercy, T., Hafizi, S., Perez, J., Fernandez-Egea, E., Suckling, J. and Jones, P. B., 2015. The impact of neuroscience on society: cognitive enhancement in neuropsychiatric disorders and in healthy people. Phil. Trans. R. Soc. B, 370(1677), p. 20140214.

Van der Crabben S N, Verhoeven-Duif N M, Brilstra E H, Van Maldergem L, Coskun T, Rubio-Gozalbo E, Berger R, De Koning T J. An update on serine deficiency disorders. Journal of inherited metabolic disease. 2013 Jul. 1; 36(4):613-9.

Wolosker H, Blackshaw S, Snyder S H. Serine racemase: a glial enzyme synthesizing D-serine to regulate glutamate-N-methyl-D-aspartate neurotransmission. Proceedings of the National Academy of Sciences. 1999 Nov. 9; 96(23): 13409-14.

Yaffe K, Sawaya G, Lieberburg I, Grady D. (1998) Estrogen therapy in postmenopausal women: effects on cognitive function and dementia. JAMA. 279(9):688-95.

Yang M, Vousden K H. Serine and one-carbon metabolism in cancer. Nature Reviews Cancer. 2016 Oct. 1; 16(10): 650-62.

Berg J M, Tymoczko J L, Stryer L. 2002. Biochemistry. 5th Edition. W.H. Freeman and Company.

Cunnane S, Nugent S, Roy M, Courchesne-Loyer A, Croteau E, Tremblay S, Castellano A, Pifferi F, Bocti C, Paquet N, Begdouri H, Bentourkia M, Turcotte E, Allard M, Barberger-Gateau P, Fulop T, Rapoport S I. 2011. Brain fuel metabolism, aging, and Alzheimer's disease. Nutrition, 27(1), 3-20.

de Koning T, Snell K, Duran M, Berger R, Surtees R. 2003. L-serine in disease and development. Biochem. J, 371, 653-661.

De Vivo D C, Trifiletti R R, Jacobson R I, Ronen G M, Behmand R A, Harik S I. 1991. Defective glucose transport across the blood-brain barrier as a cause of persistent hypoglycorrhachia, seizures, and developmental delay. New England Journal of Medicine, 325(10), 703-709.

Liu Y, Liu F, Iqbal K, Grundke-lqbal I, Gong C X. 2008. Decreased glucose transporters correlate to abnormal hyperphosphorylation of tau in Alzheimer disease. FEBS letters, 582(2), 359-364.

Pascual J M, Wang D, Lecumberri B, Yang H, Mao X, Yang R, De Vivo D C. 2004. GLUT1 deficiency and other glucose transporter diseases. European journal of endocrinology, 150(5), 627-633.

Shah K, DeSilva S, Abbruscato T. 2012. The role of glucose transporters in brain disease: diabetes and Alzheimer's disease. International journal of molecular sciences, 13(10), 12629-12655.

Wang D, Kranz-Eble P, De Vivo D C. 2000. Mutational analysis of GLUT1 (SLC2A1) in Glut-1 deficiency syndrome. Human mutation, 16(3), 224-231.

Example 5—Certain Embodiments

A1. A method of increasing or regulating glucose concentration in a central nervous system of a subject comprising administering to the subject a composition comprising a therapeutically effective amount of L-serine, or a precursor, derivative or conjugate thereof.

A2. A method of inhibiting or delaying cognitive decline in a subject comprising administering to the subject a composition comprising a therapeutically effective amount of L-serine, or a precursor, derivative or conjugate thereof.

A3. A method of enhancing cognitive function in a subject, comprising administering to the subject a composition comprising a therapeutically effective amount of L-serine, or a precursor, derivative or conjugate thereof.

A4. The method of embodiment A3, wherein memory or learning ability is enhanced in the subject compared to an amount of memory or learning ability prior to administration of the L-serine.

A5. A method of treating a disease or condition associated with a decreased level of glucose in a central nervous system of a subject comprising administering to the subject a composition comprising a therapeutically effective amount of L-serine, or a precursor, derivative or conjugate thereof.

A6. The method of embodiment A5, wherein the disease or condition is selected from the group consisting of GLUT1 deficiency syndrome, epilepsy, post-operative cognitive dysfunction, glucose-6-phosphate dehydrogenase (G6PD) deficiency, GLUT2 deficiency, GLUT3 deficiency, SGLT1 deficiency, SGLT2 deficiency, Fanconi-Bickel syndrome, glucose-galactose malabsorption syndrome, aldolase A deficiency, Downs syndrome, hypoglycemia, alcoholism, hepatitis, anorexia, insulinoma, Mild Cognitive Impairment (MCI), chemotherapy-induced cognitive dysfunction and attention deficit hyperactivity disorder (ADHD).

A7. The method of embodiment A5, wherein the disease or condition is hypoglycemia.

A8. The method of embodiment A5, wherein the disease or condition is diabetes or insulin resistance.

A9. The method of any one of embodiments A2 to A8, wherein the method comprises regulating or increasing glucose levels in the central nervous system of the subject.

A10. The method of embodiment A8, wherein the diabetes is Type I diabetes.

A11. The method of embodiment A8, wherein the diabetes is Type II diabetes.

A12. The method of any one of embodiments A1 to A6, wherein the subject is not diabetic.

A13. The method of any one of embodiments A1 to A12, wherein the subject is human.

A14. The method of embodiment A13, wherein the subject is a post-menopausal woman.

A15. The method of embodiment A14, wherein the woman is over the age of 60.

A16. The method of embodiment A13, wherein the subject is between the ages of 1 year and 21 years, or under the age of 50.

A17. The method of any one of embodiments A1 to A16, wherein the composition consists essentially of L-serine or free L-serine.

A18. The method of any one of embodiments A1 to A17, wherein the therapeutically effective amount comprises 10 grams to 100 grams of L-serine.

A19. The method of any one of embodiments A1 to A18, wherein the administering comprises administering a dose of L-serine of about 10 g/day to about 100 g/day.

A20. The method of any one of embodiments A1 to A19, wherein the composition does not contain an energy metabolism precursor.

A21. The method of any one of embodiments A1 to A20, wherein prior to the administering, the concentration of glucose in the central nervous system or cerebrospinal fluid (CSF) of the subject is less than 45 mg/dL.

A22. The method of embodiment A21, wherein after the administration the amount of glucose in the central nervous system or CSF is increased by at least 20 percent.

A23. The method of embodiment A21, wherein after the administration the amount of glucose in the central nervous system or CSF is at least 55 mg/dL.

A24. The method of any one of embodiments A1 to A23, comprising administering the composition daily for a duration of 2 to 24 weeks.

A25. The method of any one of embodiments A1 to A24, comprising administering the composition 1 to 8 times per day.

A26. The method of any of embodiments A1 to A25, wherein the therapeutically effective amount of L-serine is at a dose of about 25 mg/kg to 1,000 mg/kg body weight per day.

A27. The method of any one of embodiments A1 to A26, wherein the composition is administered orally, or by injection to the subject.

A28. The method of any one of embodiments A1 to A27, wherein the composition is in a dosage form selected from the group consisting of a chewable dosage form, a beverage formulation, a tablet, a capsule, a soft gel, a gel cap, a liquid, or a parenteral solution.

A29. The method of any one of embodiments A1 to A28, wherein the central nervous system of the subject is selected from one or more of the brain, intracranial region and cerebral spinal fluid.

A30. The method of any one of embodiments A1 to A29, wherein the L-serine is free L-serine having a purity of at least 95%.

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

Some embodiments of the technology described herein suitably can be practiced in the absence of an element not specifically disclosed herein. Accordingly, in some embodiments the term "comprising" or "comprises" can be replaced with "consisting essentially of" or "consisting of" or grammatical variations thereof. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the FIGURES, can be arranged, substituted, combined, and designed in a wide variety of different configurations, all of which are explicitly contemplated and make part of this disclosure.

What is claimed is:

1. A method for the treatment of Mild Cognitive Impairment (MCI) in a subject, the method comprising administering to the subject a composition comprising a therapeutically effective amount of L-serine, or a salt, a precursor, derivative or conjugate thereof;

wherein the subject is not diagnosed with and/or does not have Amyotrophic Lateral Sclerosis (ALS), Alzheimer's disease (AD), Amyotrophic Lateral Sclerosis/Parkinsonism Dementia Complex (ALS/PDC), dementia, Parkinson's Disease (PD), Huntington's disease (HD), Progressive Supranuclear Palsy (PSP), and/or Lewy Body Dementia (LBD); and wherein prior to the administering, the concentration of glucose in the central nervous system or cerebrospinal fluid (CSF) of the subject is less than 45 mg/dL, and after the administration the concentration of glucose in the central nervous system or CSF is (i) increased by at least 20 percent or (ii) increased to an amount of at least 55 mg/dL.

2. The method of claim 1, wherein memory or learning ability is enhanced in the subject compared to an amount of memory or learning ability prior to administration of the L-serine or a salt, a precursor, derivative or conjugate thereof.

3. The method of claim 1, wherein the method comprises regulating or increasing glucose levels in the central nervous system of the subject.

4. The method of claim 1, wherein the subject is not diabetic.

5. The method of claim 1, wherein the subject is human.

6. The method of claim 1, wherein the subject is a post-menopausal woman or a woman over the age of 60.

7. The method of claim 1, wherein the subject is between the ages of 1 year and 21 years, or under the age of 50.

8. The method of claim 1, wherein the composition consists essentially of L-serine or free L-serine.

9. The method of claim 1, wherein the therapeutically effective amount comprises 5 grams to 100 grams of L-serine or a salt, a precursor, derivative or conjugate thereof.

10. The method of claim 1, wherein the administering comprises administering a dose of about 5 g/day to about 100 g/day of L-serine or a salt, a precursor, derivative or conjugate thereof.

11. The method of claim 1, wherein the composition does not contain an energy metabolism precursor.

12. The method of claim 1, comprising administering the composition daily, 1 to 8 times per day, for a duration of 2 to 24 weeks.

13. The method of claim 1, wherein the therapeutically effective amount of L-serine or a salt, a precursor, derivative or conjugate thereof is administered at a dose of about 25 mg/kg to 1,000 mg/kg body weight per day.

14. The method of claim 1, wherein the composition is administered orally in a dosage form selected from the group consisting of a chewable dosage form, a beverage formulation, a tablet, a capsule, a soft gel, a gel cap, and a liquid.

15. The method of claim 1, wherein the composition comprises free L-serine having a purity of at least 95%.

* * * * *